United States Patent [19]

Ribi

[11] Patent Number: 5,342,692
[45] Date of Patent: Aug. 30, 1994

[54] LIPID-PROTEIN COMPOSITIONS AND ARTICLES AND METHODS FOR THEIR PREPARATION

[75] Inventor: Hans O. Ribi, Atherton, Calif.

[73] Assignee: Biocircuits Corporation, Sunnyvale, Calif.

[21] Appl. No.: 41,278

[22] Filed: Mar. 30, 1993

Related U.S. Application Data

[63] Continuation of Ser. No. 697,219, May 7, 1991, abandoned, which is a continuation of Ser. No. 321,962, Mar. 10, 1989, Pat. No. 5,087,952.

[51] Int. Cl.$^5$ .............................................. B32B 7/04
[52] U.S. Cl. .................. 428/420; 422/82.05; 428/446; 428/450; 428/451; 428/515; 435/175; 435/176
[58] Field of Search ............ 428/446, 450, 451, 474.4, 428/420, 515; 435/175, 176; 357/23.1, 23.7; 422/82.05

[56] References Cited

U.S. PATENT DOCUMENTS

| | | | |
|---|---|---|---|
| 4,193,983 | 3/1980 | Ullman et al. | 424/12 |
| 4,489,133 | 12/1984 | Kornberg | 428/408 |
| 4,562,157 | 12/1985 | Lowe et al. | 435/291 |
| 4,859,538 | 8/1989 | Ribi | 428/474.4 |
| 4,881,109 | 11/1989 | Ogawa | 435/176 X |

FOREIGN PATENT DOCUMENTS 2173039  10/1986  United Kingdom .................. 357/17

*Primary Examiner*—Paul J. Thibodeau
*Assistant Examiner*—H. Thi Lê
*Attorney, Agent, or Firm*—Bertram I. Rowland

[57] ABSTRACT

Novel articles are provided comprising at least one polymerized surfactant layer and at least one protein layer specifically bound to the surfactant layer. Depending upon the nature of the preparation of the layers, the layers may be formed as a plurality of substantially parallel layers, filaments, tubes, helices or other complex assembly. The articles may be used for improved determination of protein structure, electronic devices, enzyme reactors and in biosensors. Improved methods are provided for electron microscopic analysis of proteins.

6 Claims, 5 Drawing Sheets

LIPID-PROTEIN COMPOSITIONS AND ARTICLES AND METHODS FOR THEIR PREPARATION

This is a continuation of application Ser. No. 07/697,219 filed May 7, 1991 now abandoned which is a continuation of application Ser. No. 07/321,962, filed Mar. 10, 1989 now U.S. Pat No. 5,087,952.

FIELD OF THE INVENTION

Polymerized surfactant-protein compositions and methods of their preparation are provided for determining protein structure, providing for biosensors, enzyme reactors and molecular electronics, and for providing orderly arrays of proteins as base layers. Various parameters are employed for achieving a variety of structural elements.

BRIEF DESCRIPTION OF THE BACKGROUND

In a universe where conditions direct substances to have a substantial degree of disorder, there is a continuing interest in developing new techniques for ordering molecules for a wide variety of purposes. In the field of electronics, the ability to develop crystalline arrays having a low level of imperfections has permitted ever increasing sophistication and efficiency in the handling of electronic circuits. As efforts have been made to increase the amount of information which may be stored or manipulated within a particular volume or area, difficulties in defining specific elements and preventing the interaction between adjacent elements has greatly increased.

There is also substantial interest in being able to determine structures of complex macromolecules. With proteins, it is frequently difficult to obtain crystalline structures to permit structural determinations using x-ray diffraction or two-dimensional crystals for use in electron crystallography.

Other areas where order is of interest include structural members, such as fibers, layers in multilamellar constructions, and the like.

There is also substantial interest in being able to produce novel conducting materials, semiconductor materials and insulating materials, particularly those that have properties which may be different from other materials having analogous characteristics. The ability to employ switches whose function can be modified by external conditions is of particular interest and can have a wide variety of applications.

BRIEF DESCRIPTION OF THE RELEVANT LITERATURE

U.S. Pat. No. 4,489,133 describes procedures and compositions involving orderly arrays of protein molecules bound to surfactants. Thomas et al., *Electron. Letters* (1984) 20:83–84 describe a GaAs/LB film MISS switching device employing ω-tricosenoic acid as the surfactant bilayer for producing a thin insulator. Lochner et al., *Phys. Status Solidi* (1978) 88:653–661 describe photoconduction in polydiacetylene multilayer structures and single crystals. Sugi, *J. Molecular Electronics* (1985) 1:3–17 provides a review of Langmuir-Blodgett film use in electronics. Reynolds, ibid (1986) 2:1–21 describes conducting organic polymers. Wilson, *Electron. Letters* (1983) 19:237 describes the principles of a three dimensional molecular electronic memory employing polydiacetylene crystals or Langmuir-Blodgett multilayer films. Descriptions of electronic devices employing organized macromolecular ensembles formed with surfactant layer crystallization include Arrhenius et al., *Proc. Natl. Acad. Sci. USA* (1986) 83:5355–5359; Haddon and Lamola, ibid (1985) 82:1874–1878; and Paleos, *Chem. Soc. Rev.* (1985) 14:45–67. Biosensors employing surfactant layer crystallization are described by Owen, *Ann Clin. Biochem.* (1985) 22:555–564 and Thompson and Krull, *Trends in Anal. Chem.* (1984) 3(7):173–178. Bader et al., *Advances in Polymer Sci.* (1985) 64:1–62 describe polymeric monolayers in liposomes as models for biomembranes. See particularly, pages 22 to 25 describing polymerized vesicles.

SUMMARY OF THE INVENTION

Novel articles are provided comprising at least two layers: (1) a polymerized surfactant monolayer having long polymeric strands in a substantially ordered array; and (2) a protein layer bound to the surfactant monolayer in a substantially ordered array. By varying conditions in the preparation of the article, the conformation of the article can be varied from substantially parallel multilayers to tubes, filamentous arrays, helices or other complex assemblies. Parameters affecting the molecules (surfactants-protein) which comprise the assemblies may be altered in order to modulate the intrinsic physical properties of the assembly. The articles can find use in protein structure determination, electronics, biosensors, etc. Improved methods for producing ordered protein arrays are also provided.

DESCRIPTION OF THE SPECIFIC EMBODIMENTS

Figure 1:
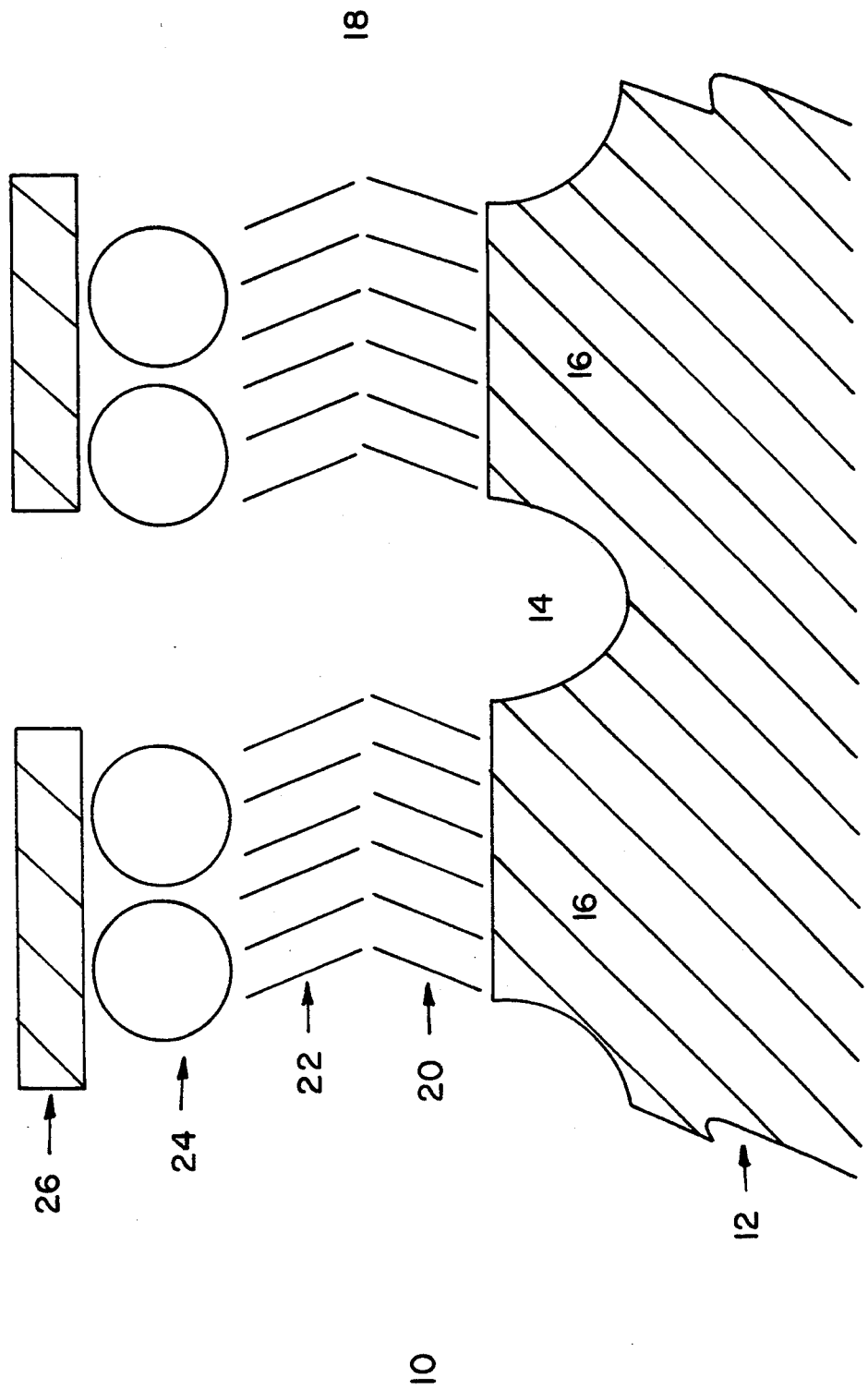
FIG. 1 is a diagrammatic view of a switching device.
Figure 2:
FIG. 2 is an electron micrograph of cholera toxin crystals on layers of GM1 and polymerized tricosa-10,12-diynoic acid (1 cm is roughly 1000 Å)
Figure 3:
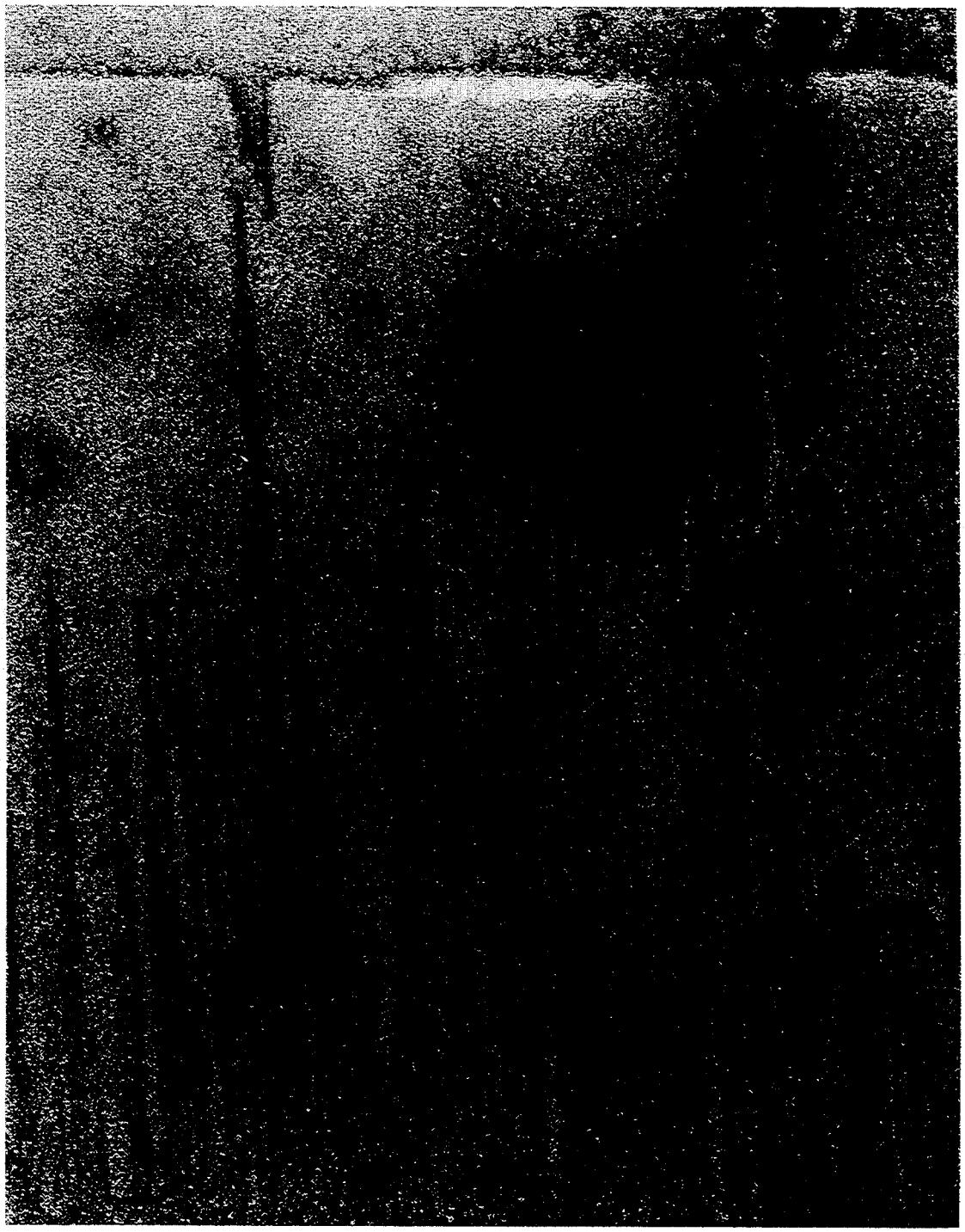
FIG. 3 is an electron micrograph of polymer filaments extending from crystals of chlolera toxin on GM1 and polymerized tricosa-10,12-diynoic acid layers (1 cm is roughly 1000 Å)

Articles are provided and methods for their preparation, where the articles are characterized by having at least two layers: (1) an ordered polymerized surfactant monolayer; and (2) an ordered protein monolayer bound to said surfactant monolayer by forces stronger than van der Waal forces. By ordered is intended molecules in a regular lattice.

The articles may have two or more layers, there generally being from about 1 to 1000, more usually 1 to 100 surfactant layers, generally 1 to 10 layers, particularly 1 to 3 layers, while from 1 to 3, more usually 1 to 2 protein layers. The surfactant layers will generally be from about 10 Å to 1μ in thickness or more, more usually from about 20 Å to 0.5μ in thickness. The protein will generally be from about 25 to 1,000 Å in thickness, usually from about 25 to 600 Å in thickness. Depending upon the nature of the article and the conformation of the surfactant layer and the protein layer, thicknesses may be varied widely.

The conformation of the article may be varied depending upon the manner in which it is produced. For some purposes, the layers will be stacked in substantially parallel layers, which layers may be planar or have a repeating cycle. Alternatively, the articles may have individual tubular structures which may be independent or linked by covalent or non-covalent means, where the tubes will normally have an internal protein monolayer, a surfactant layer, which may be mono- or multilamellar, and a protein layer which may be mono- or multilamellar. A third configuration is a helical configuration, where the surfactant layer and protein layer for an entwined helix, with the appearance in an electron micrograph of being wrapped around each other.

The surfactant layers may be crystalline, amorphous, or smectic crystals, conducting or non-conducting, depending upon the nature of the surfactant or surfactant mixture employed for preparing the surfactant layer. If desired, the compositions of successive surfactant layers may be varied, though for the most part the multilamellar surfactant layers will be of substantially uniform composition.

The substantially parallel layered articles will usually have a minimum planar dimension of 5 Å, particularly as a linear polymer. For the most part, the surface areas of a layer will usually be in range of about 10 Å$^2$ to about 1 m$^2$. The tubular structures will generally range from about 25 to 1$\mu$ in diameter, will usually be at least about 500 Å in length, more usually at least about 5$\mu$ in length. Helical structures generally range from about 300 to 1,000 Å, in particular cases structures having varying thicknesses of from about 200 to 2000 Å, in one example being observed at both about 400 Å and at about 800 Å. The length of the helix will generally be at least about 0.1$\mu$, usually at least about 1$\mu$, and may be 3$\mu$ or more, although lengths greater than about 100$\mu$ are not observed.

New articles of this invention may be modified in a wide variety of ways. Cross-linking may be provided, where the articles may be stacked one above the other, or cross-linked in lateral dimensions, so as to provide arrays of tubes or helical filaments. Cross-linking can be achieved in a variety of ways, both covalent or non-covalent. Cross-linking agents include glutaraldehyde, maleimidobenzoic acid, methyldithioacetic acid, diazobenzoic acid bisulfite, antibodies, avidin, where biotin may be bound to the protein or surfactant, etc. Thus, relatively large articles can be produced which can be readily manipulated and used in a variety of ways.

The composition of the surfactant layer may be varied widely. The composition may be homogeneous, where the binding surfactant is polymerizable and has a polar terminus which may serve as a ligand for a complementary binding protein, or heterogeneous where the binding surfactant may or may not be polymerizable. The ligand surfactant may be diluted with a polymerizable surfactant. Various functional groups may be present to provide for polymerization. Illustrative groups include triple bonds, monoynes, diynes, dienes, pyrroles, vinyl esters, vinyl ethers, acrylates, vinyl aromatics, where the polymerizable functionality is part of the surfactant chain or is attached to a surfactant chain. For the most part, the surfactant chains will be aliphatic chains of at least 6, usually at least 12 carbon atoms and not more than about 30 carbon atoms, preferably being from about 14 to 26 carbon atoms, more preferably from about 16 to 24 carbon atoms. While the unsaturated functionalities may be linked to an activating functionality, such as carbonyl, oxy, aryl or the like, usually the polymerizable functionalities will be separated from both the polar and non-polar terminus, usually by at least 1 carbon atom and generally from about 1 to 14 carbon atoms, more usually from about 1 to 12 carbon atoms.

Polymerizable surfactants have been extensively described in the literature as is evidenced by the articles described above, whose disclosure relevant to the preparation and use of polymerizable surfactants and the references cited therein, are incorporated herein by reference.

A wide variety of surfactants may be employed, either by themselves or in combinations, where the surfactant which provides for the specific binding will be present in at least about 0.1%, usually about 5% and may be present up to 100%, more usually from about 5% to 80%, desirably from about 10% to 60%, more desirably from about 20% to 50%. The surfactants may be salts, esters, either organic or inorganic, amides, ethers, alcohols, cations, e.g. quaternary ammonium, or the like. The polar group may be a carboxy salt, particularly multivalent salt, e.g. cadmium, lead, barium, cobalt, manganese, etc., a sugar, an organic salt, e.g. betaine, phosphate ester, e.g. phosphatidyl glycerol, serine, inositol, etc. Naturally occurring, synthetic surfactants, or combinations thereof, which may be employed in the formation of the surfactant layer include stearate, oleate, linoleate, arachidonate, arachidate, vinyl stearate, $\omega$-tricosenoic acid, pentaeicosa-10, 12-diinoic acid, $\omega$-3'-pyrrolyloctadecanoate, cholesterol, gangliosides, sphingomyelins, cerebrosides, etc.

For the most part, mixtures will be used where the specific binding surfactant, which may or may not be capable of addition polymerization, will be diluted with the surfactant capable of polymerization and in some instances other surfactants as well to provide for specific properties. For example, cholesterol may be added to introduce cholesteric properties into the surfactant layer. For the most part, the mixtures will not have more than about 6 different surfactants, usually not more than about 4 different surfactants and usually having from 2 to 3 different surfactants. Of particular interest are those surfactants where the fatty acids are joined to phosphatidylcholine or phosphatidylethanolamine. Alternatively, condensation polymerizable surfactants may be used, e.g. amino acids, using water soluble carbodiimides as activators.

The protein layer bound to the surfactant layer may be any protein which specifically binds to another molecule. Thus, the proteins may be immunoglobulins, natural surface membrane receptors, such as growth factor receptors, G-proteins, neurotransmitter receptors, etc., blood protein receptors such as thyroxine-binding globulin, enzymes, proteins which recognize sugars, such as lectins, toxins, proteins which recognize nucleic acids, such as histones, DNA and RNA polymerases, depressors, etc. Thus, there is a rich availability of proteins which recognize specific structures which can be joined to surfactants in a variety of ways to provide for specific binding.

While the first layer requires a specific binding between the ligand bound to the surfactant and the protein, various techniques can be used to add additional protein layers, such as functionalizing the first protein layer with, for example, biotin, and then providing a second layer of avidin. Alternatively, antibodies can be employed which bind to the first layer or other specific proteins which bind to the first protein layer, for example, Staphyloccus aureus protein A or rheumatoid factor with immunoglobulins. Thus, extended arrays can be obtained if desired, where one wishes to have a plurality of protein layers.

The articles of this invention can be prepared, for the most part, using conventional techniques employing particular conditions to achieve the desired structure. For the most part, Langmuir-Blodgett techniques will be employed as described in the references cited previously. In employing the subject methods, attention should be given to the experimental section for guidance as to the particular range that should be used with any particular parameter for the desired result.

A large number of parameters are available which can be used to influence the nature of the product. These parameters include the buffer, including pH, ionic strength, cations employed, e.g. mono- or polyvalent, composition of the surfactant, both as to the polymerizable surfactant and the non-polymerizable surfactant, including such considerations as chain length, the situs of the polymerizable functionality, the nature of the polymerizable functionality, and the nature of the polar head group; the manner in which the surfactant layer is formed, including concentration of surfactant and solvent, the nature of the solvent, the spreading method, and the amount of surfactant employed, which will affect the availability for multilamellar layers; and physical parameters, such as film tension, crystallization time, temperature, humidity, and E (electric) field, M (Magnetic) field (protein dipole moment). Also, there is the opportunity to introduce various agents into the aqueous medium which can affect the nature and conformation of the article, e.g. specific ions, organic or inorganic.

An aqueous medium is formed, which is normally buffered at a pH in the range of about 4 to 9, preferably from about 5 to 9. The salt concentration will generally be in the range of about 10 mM to 1 molar. Illustrative buffers include phosphate, borate, barbitone, carbonate, Tris, MOPS, MES, etc. Illustrative buffer compositions include phosphate buffered saline; 138 mM NaCl, 50 mM potassium phosphate, pH 7.2; 200 mM sodium borate, pH 8.2. It is found that PBS favors monolayers, cadmium stabilizes the layer, while borate favors multilayer packing. In addition, various organic cations may be added such as polyamines, where the amino groups tend to be separated by at least 2 carbon atoms and not more than about 12 carbon atoms. Illustrative compounds include sperimine, spermidine, nopaline, octopine, etc. The presence of the polyvalent organic cations, as well as relatively high levels of inorganic cations, e.g. 50 mM magnesium, or higher, will favor helical structures and paracrystalline arrays. The concentration of the multivalent cations will depend to some degree upon the nature of the cation, generally ranging from about 0.1 to 200 mM, more usually from about 10 to 100 mM and will be included in the determination of total salt concentration.

The protein may be introduced into the aqueous medium either before or after formation of the surfactant layer. When it is introduced after formation of the surfactant layer, it will be injected carefully below the surfactant layer from the side, so as not to disturb the orientation of the surfactant layer. The concentration of the protein will vary widely, usually being at least stoichiometric with the amount of available complementary ligand. That is, where the surfactant layer is homogeneous having only ligand bound surfactant, only a proportion of the total ligand will be available for binding. Depending on the nature of the protein, this will generally vary rom about 0.1 to 0.5 of the total ligand available. If desired, substantial stoichiometric excess may be employed, usually about 1.5 stoichiometric, more usually about 2. The excess may be five-fold or higher. The amount employed will also be affected by the binding affinity of the protein for the ligand, the size of the protein, the effect of the number of protein molecules on the nature of the order of the array, and the like. Generally, concentration of protein will be from about 10 $\mu$g/ml, not more than 5 mg/ml, more usually not more than about 1 mg/ml, more usually in the range of about 500 $\mu$g/ml.

In preparing the surfactant layer, surfactant will be dissolved in a convenient non-polar volatile solvent. Illustrative solvents include chloroform, hexane, isopropyl ether, methylenedichloride, benzene, etc. Individual solvents or combinations may be employed, depending upon the nature of the surfactant. Trace amounts of an organic hydrophillic solvent may be employed, when necessary to solublize a particular surfactant. The concentration of surfactant will generally be from about 0.01 to 5, more usually about 0.1 to 1 mg/ml.

The aqueous medium may be in any convenient container, particularly a plastic container, such as Teflon, PVC, Delrin, glass or metal. Various containers are available for the formation of surfactant monolayers which allow for the control and monitoring of film pressure. The surfactant will usually be maintained at at least the maximum equilibrium spreading pressure and up to the collapse pressure.

It may be desirable to add the protein slowly to the surfactant layer. In this way, the size of the ordered or crystalline domains may be enhanced. One way to achieve this result would be the slow control of addition of protein, using various types of pumps or motorized controlled syringes for introducing the protein into the buffered aqueous medium. Alternatively, one may use two wells joined by a bridge, e.g. a bibulous layer, which allows for transfer of surfactant from one well to the other. By spreading surfactant in one well and having the aqueous protein containing buffered medium in the other well, the surfactant may be transferred at a controlled rate from the first well to the second well by forming ordered surfactant layers and then continuously increasing the pressure forcing the surfactant to migrate across the bridge to the other well. By monitoring and controlling the pressure in the second well, an ordered layer can be maintained, which will react with protein in the aqueous buffered medium as it spreads on the surface in the second well.

The surfactant layer will initially be held at at least the maximum equilibrium spreading pressure, but may be changed, higher or lower during protein binding, while still maintaining a condensed surfactant phase.

The system will now be incubated for at least about 5 minutes to insure reaction between the protein and the surfactant. Usually the reaction will not require more than 48 hours, more usually not more than about 24 hours. In this period, the protein will bind and become ordered, where the protein may assume its lowest thermodynamic state as bound to the surfactant. A humid atmosphere is normally maintained during the reaction.

Depending upon the nature of the polymerizable functionality, the surfactant may now be polymerized. The polymer may have as few as 3 units or may have $10^7$ or more units. Alternatively, the surfactant could be polymerized prior to contact with the protein if desired. In either event, the same techniques for polymerization would be used. Preferably, polymerization is carried out after conjugation with the protein. Polymerization may be achieved by employing short wave ultra violet light, e.g. below 300 nm, with diynes, in the range of about 230 to 275 nm, X-rays, free radicals, redox agent, or other convenient initiator. For the most part, the polymers will be addition polymers rather than condensation polymers, although condensation polymerization may be employed as indicated previously. The time for the polymerized, for example irradiation, will be at least about 1 min., and usually not more than about 60 min., frequently not more than about 30 min. Upon completion of the polymerization, the article is now formed and may be used in a variety of ways, depending upon its conformation.

Where a multilamellar surfactant layer is desired, this can be achieved by employing an excess of surfactant over that required for monolayer. Thus, by raising the pressure to just below the maximum equilibrium spreading pressure, generally less than about 10% below the maximum equilibrium spreading pressure, mono- or multilamellar films can be obtained. Alternatively, successive dippings using Langmuir-Blodgett methods may be employed for multilayers.

It is found that the lateral surface tension of the surfactant layers exerts similar effects on crystallization of antibodies, ribonucleotide reductase and cholera toxin, indicating relatively low dependence on protein type. By contrast, the concentration of surfactant-ligand in the surfactant layers and the type of other surfactant lacking ligand (filler surfactants) had varying effects on array formation among the different proteins.

The temperature for the reaction may vary widely, generally being below about 60° C., preferably being below about 40° C., usually ranging from about 0° C. to 30° C., more usually from about 4° C. to 30° C.

The subject method can be used without polymerizable surfactants and polymerization to obtain improved ordered protein arrays.

Once the structure has been formed, as already indicated it may be modified by cross-linking, covalently or non-covalently, using various polyfunctional agents, e.g. immunoglobulins, cross-linking agents, high energy irradiation, or the like. The article may be retrieved in a variety of ways. Vertical dipping may be employed, where a solid substrate may be introduced into the aqueous medium while the film is maintained under pressure, so as to coat the solid substrate as it enters and is retrieved from the aqueous medium.

Alternatively, horizontal lifting methods can be employed, where the substrate is held horizontally and is lowered onto the monolayer on the water surface from above. Alternatively, the substrate may be immersed in the water before the spreading of the monolayer and contact is made with the protein layer, as the substrate is raised through the aqueous medium comes in contact with the protein layer. The techniques include the monomolecular, the sweeping technique, use of polymers such as polyvinyl alcohol to provide a polymeric coating, which may then be removed with water, or the like.

The subject articles are found to have a high degree of stability for use in electron microscopy. Thus, the subject articles are substantial improvements over other techniques which have been previously described to obtain electron micrographs of organized linear protein arrays. For this purpose, carbon-coated electron microscope (EM) grids are contacted with the hydrophobic tails of the surfactant adjacent the air/water interface, the grids removed and stained for electron microscope investigation.

The subject articles, being surfactant polymer layers decorated with enzymes, may be used in the construction of highly efficient enzyme reactors. The polymer surface, when saturated with specifically bound enzyme, will yield the maximum concentration of catalyst in two dimensions. Because of the high degree of structural integrity these assemblies may be placed in rapid flow devices in a variety of orientations without suffering structural damage.

The subject articles may also be used in a variety of electronic sensors and devices. A particular application is described by Thomas et al. (1984) supra, where the subject article comprising the composite surfactant-protein layers may be substituted for the thin insulator described by Thomas. Similarly, the subject layers may be used as substitutes for the polydiacetylenes described by Wilson, (1983) supra. In the Wilson article, Wilson describes the ability to read energy into the system and read out fluorescence. By having proteins present, by varying the medium in which the protein is in contact, changes in the conformation of the protein will result in changes in the electronic nature of the polymeric surfactant layer. Thus, variations in wave length of the emitted light can be related to specific materials present in the medium.

The variations in the conformation of the proteins could be as a result of a variety of effects. For example, with enzymes, binding of substrates or inhibitors could result in a change in conformation. For a large variety of proteins, allosteric effects are involved, particularly proteins which regulate various nucleic acid processes, such as replication and transcription. Also, enzymes are known to be subject to allosteric effects. In addition, various membrane proteins or membrane binding proteins, particularly receptors, will be subject to modification upon binding to ligand. The possibilities include membrane associated proteins, e.g. cholera toxin, water soluble proteins and integrated membrane proteins, e.g. ion channel proteins, and nucleic acid binding to proteins, such as histones, polymerases, repressors, or the like.

A device which may be considered is depicted in FIG. 1. Device (10) is a semiconductor layer (12), which is etched to define wells (14) and islands (16), to provide insulation for individual islands. By appropriate polarization, each of the islands may be insulated from the other islands. Mounted on the surface of each of the islands (16), is a surfactant layer with a dilamellar layer being depicted (18) have a first layer (20) and a second layer (22), where the second layer (22) contains the ligands (ligands may be in one or more layers). Protein layer (24) is bound to the ligands of second layer (22) to define in this example, a protein insulating layer which separates metal layer (26) from the polymerized surfactant layer (22). Layer (20) may be the same as layer (22) and may provide a polymerized layer or non-polymerized layer, usually being a polymerized layer. The thin metal may be evaporated onto the protein layer to provide for a conductor.

In practicing the invention, a potential is provided across semiconductor (12) and metal layer (26). Light pulses may then be introduced which are transmitted through metal layer (26) and penetrate to at least surfactant layer (22). Depending upon the composition of the surfactant polymer layer, the fluorescent light emitted by the electronic array will vary. Thus, by subjecting the proteins to various molecules, such as effector ions or the like, or varying physical parameters which may affect their conformation, one can modulate a change in wavelength of the observed fluorescent light. Furthermore, by isolating the individual island arrays, one from the other, each of the arrays may be subjected to different media and individually interrogated by irradiating an individual array with light, while maintaining the other arrays in the dark.

The subject articles can be used a photoconductors, as described by Lochner et al., Phys. Stat. Sol. (1978) 88:653–661. The presence of the proteins stabilize the structure of the conductive polymers and provide insulation of the polymeric chains, and can be used to modulate the photoconduction by virtue of their response to temperature, various media, or agents in the media which may bind, specifically or non-specifically, to the proteins.

Dealing with tubular arrays or helices, where the tubular arrays or helices aggregate, various techniques may be employed for separating individual members, so as to provide for interactions with the individual members. For example, the arrays may be placed on an ice surface, where the ice forms a convex layer. It is found that the surface tension will provide for separation of the individual members. The separated ends may then be bound to a conductive or semiconductive surface and may be individually interrogated by light pulses. In this manner, the presence or absence of light at a particular site may be determined, which can be used for the manipulation of information.

The following examples are offered by way of illustration and not by way of limitation.

EXPERIMENTAL

Studies with the E. coli B1 dimer of Ribonucleoside Diphosphate Reductase Surfactants For synthesis of dATP-aminocaproyl-PE (PE-dioleoylphosphatidylethanolamine), the triethyl ammonium salt of 2'-deoxy-5'-adenosine triphosphate was activated with dicyclohexylcarbodiimide and allowed to combine with aminocaproyl-PE. Other surfactants were purchased from Avanti Polar Lipids.

Surface Pressure Measurements

Teflon or glass troughs (1 mm depth, 3cm$^2$ surface area) were filled with water or buffers and varying amounts of dATP-aminocaproyl-PE and egg PC (phosphatidylcholine) (0.5 mg/ml, chloroform:hexane 1:1 (v/v)) were applied to the surface. Lateral pressures were monitored with time by the Wilhelmy plate method (Möbius et al., Ber. Bunsenges. Phys. Chemil. (1969) 73:845.

Crystallization Trials

Drops of B1 (E. coli B1 subunit of ribonucleoside diphosphate reductase) solution (1–3 μg of protein in 12 μl of buffer) in teflon wells (4 mm in diameter, 1 mm deep) were coated with surfactant mixture (0.25–0.5 μl, 0.5 mg/ml in chloroform:hexane, 1:1 (v/v)) and kept in a humid atmosphere at 4°–30° C. Buffers contained 100 mM NaCl, 1–100 mM MgCl$_2$, 2 mM dithiothreitol, and either 25 mM MES-Na$^+$, pH 5.4–6.9, or 25 mM Tris-HCl, pH 7.1–8.8. After 1–14 days, carbon-coated electron microscope grids were touched to the surface, washed with one drop of water or 10 mM Tris-HCl, pH 7.4, and stained with 1% uranyl acetate.

The formation of surfactant layers containing dATP-aminocaproyl-PE was monitored by measurements of surface pressure at the air-water interface. Monolayers of pure dATP-aminocaproyl-PE spread on water showed a similar pressure area profile to dioleoylphosphatidylcholine (dioleoyl PC), with collapse upon compression to about 48 dynes/cm. Salts in the subphase (0.1–0.3M NaCl, neutral pH, with or without 5 mM MgCl$_2$) caused instability of dATP-aminocaproyl-PE layers spread on a fixed surface area. Collapse occurred within minutes of formation at all pressures tested (13–48 dynes/cm). The difficulty was overcome by adding other surfactants. A mixture of egg PC and dATP-aminocaproyl-PE in a 9:1 molar ratio formed monolayers as stable as those of pure egg PC, and films of this composition were used to crystallize the B1 dimer.

Crystals were formed at the air-water interface. Drops of B1 solution (2–3 μg of B1 protein in 12 μl solution containing 100 mM NaCl, 15 mM MgCl$_2$, 15 mM spermidine, 1.5 mM dTTP) in teflon wells were coated with surfactant mixture, kept in a humid atmosphere at 23° for 1–46 hrs, and examined by touching the surface with a carbon-coated grid, washing, negative staining, and electron microscopy (Philips 201 transmission electron microscope). Within hours, linear arrays appeared which showed some tendency to pack side by side but little long range order. After 20 hrs, two-dimensional crystals were observed. Omission of dATP-aminocaproyl-PE or the addition of 1.5 mM dATP gave no crystals, and no evidence of protein binding (a studded appearance of the surfactant layers). Omission of dTTP gave fewer ordered arrays even upon longer incubation. Arrays formed at pH values between 5.7 and 8.0, with an optimum in the degree of order near pH 7.4. Under more acidic conditions, the surfactant layers appeared distorted, while under more alkaline conditions, there was extensive protein binding but no ordered arrays. The composition of the surfactant layers was crucial. Substitution of egg PE for PC gave protein binding but no ordered arrays. Egg monomethyl and dimethyl PE gave arrays, but the degree of order appeared less than with PC.

Crystals gave optical diffraction patterns that could be indexed on a rectangular reciprocal lattice, with unit cell parameters of a=277 Å, b=110 Å, and γ=90°. The diffraction extended to a 37 Å resolution. Filamentous arrays and helical bundles of filaments were favored with increasing amounts of magnesium (≦100 mM) in the buffers.

Image analysis (Amos et al., Prog. Biophys. Molec. Biol. (1969) 39:183–231) of rectangular crystals was carried out with 38 independent reflections. Fourier synthesis gave "noise-filtered" images showing features suggestive of two-fold rotational symmetry. On refining the origin of the reciprocal lattice by minimizing the differences in phase between two-fold related reflections, an average differences from centro-symmetric phases of 12° was obtained for seven averaged data sets. Fourier synthesis gave a symmetry-averaged image showing four elongated protein densities in the unit cell, each about 110 Å long and 32 Å in width. Two objects paired together, suggesting, based on these dimensions, that a pair of objects is a B1 dimer.

STUDIES WITH CHOLERA TOXIN B SUBUNIT

MATERIALS AND METHODS

Materials

Cholera toxin B subunit, purified from culture filtrates of *V. cholerae* strain 569B by affinity chromatography (Toyot et al., *Eur. J. Biochem.* (1981) 113: 249–258), was provided by the Institute Merieux, Marcy, France. B subunit was also purchased from Sigma Chemical Co. Egg phosphatidylcholine and dioleoylphosphatidylethanolamine were from Avanti Polar Lipids, Inc., and ganglioside GM1 was from Supelco. Bis(sulfosuccinimidyl)suberate and dimethylsuberimidate were from Pierce Chemical Co. and Sigma Chemical Co.

Crystallization, Electron Microscopy and Image Analysis

Surfactant layers were spread at the air-water interface by applying 1.2 μl of surfactant solution (0.5 mg/ml in chloroform:hexane, 1:1 by volume) to the surface of a 50 μl drop of aqueous solution (10 mM Tris, 150 mM NaCl, pH 7.3) containing B subunit (250 μg/ml solution) in a teflon well. After 4 to 48 h at room temperature, a carbon coated electron microscope grid was brought in contact with the drop, and the grid was washed with buffer and stained with 1% uranyl acetate. Micrographs were recorded with minimal electron doses on a Philips EM 400 microscope operating at 100 kV. Optical diffraction was used to assess the quality of the images. Image processing was performed according to Amos et al., *Prog. Biophys. Molec. Biol.* (1982) 39: 183–231.

Chemical Cross-Linking

B subunit (40 μl of a 1.0 mg/ml solution in 0.2M sodium borate, pH 8.5), was treated with various concentrations of bis(sulfosuccinimidyl)suberate at room temperature. After 45 min, the mixture was boiled for 10 min and cross-linked products were resolved by electrophoresis in an SDS-15% polyacrylamide gel (Weber and Osborn, *J. Biol. Chem.* (1969) 244:4406–4412). Alternatively, 0.4 ml of B subunit (1 mg/ml) was mixed with 0.6 ml of liposomes (egg phosphatidylcholine: GM1, in a 9:1 molar ratio, sonicated for 5 min in a bath-type sonicator at 2 mg of total surfactant per ml in 0.2 M sodium borate, pH 8.5) and, after 30 min at room temperature, the mixture was cross-linked.

RESULTS

Two-Dimensional Crystals of B Subunit-Ganglioside Complexes

Surfactant layers were prepared from dioleoylphosphatidylethanolamine or egg phosphatidylcholine, mixed with 10 mole % GM1, by coating the mixture on drops of aqueous solution. Five to ten-fold more surfactant was used than necessary to form a monolayer, to ensure the maintenance of maximum equilibrium spreading pressure of the surfactant film, a condition for optimal yields of ordered protein arrays. B subunit was present in the aqueous solution before application of the surfactant mixture or, alternatively, it was injected beneath the surface of preformed surfactant layers to avoid denaturation of protein at the air-water interface. Protein binding occurred rapidly (shown by a studded appearance of surfactant layers in the electron microscope), followed by crystallization within 6 h at room temperature. The largest crystalline areas were obtained with phosphatidylethanolamine-containing films after about 24 h of incubation. Typically, 10–20% of the surface of an electron microscope grid was covered with crystals up to 15μ on a side.

Projected Structure of the B Oligomer

Two crystal forms were revealed by optical diffraction from electron micrographs, a rectangular lattice (unit cell dimensions a=120 Å, b=131 Å, γ−90°), which gave diffraction extending to a ninth order reflection at 15 Å resolution and a hexagonal lattice (unit cell dimension 68 Å) which gave four orders of diffraction, corresponding to 19 Å resolution. The proportion of the two crystal forms varied, with no discernible dependence of pH, ionic strength, time or temperature.

Projected structures were computed with the use of 38 and 15 independent reflections from the rectangular and hexagonal lattices, corresponding to 17 and 28 Å resolution. (Origin refinement gave average and root mean square phase residuals of 12.5° and 8.0° in the two cases.) The structures showed rings of five or six protein densities, nearly identical in outer diameter (60 Å), inner diameter (20 Å), and distance from the center of the right to a peak of protein density (20 Å).

Chemical Cross-Linking of the B Oligomer

The occurrence of two crystal forms, apparently containing different oligomeric structures of the B subunit, was reinvestigated by chemical cross-linking. In previous studies with dimethyl suberimidate as cross-linking reagent, five bands were resolved in SDS-polyacrylamide gels, indicative of a pentameric structure (Cull, *Biochem.* (1976) 15:1242–1248). With bis(sulfosuccinimidyl)suberate, a pattern of six bands was obtained whose mobilities in SDS-polyacrylamide gels fall on a smooth curve in a semilog plot against the molecular weights of B polypeptide monomer through hexamer. Similar results were obtained at pH 8.5 or 9.0, and with B oligomers either free in solution or bound to GM1 in liposomes. Extensive reaction with dimethyl suberimidate gives a sixth band as well, although less distinct than that found with bis(sulfosuccinimidyl)suberate. These results are consistent with the occurrence of a hexameric form of the B subunit.

Two-Dimensional Crystals of Cholera Toxin

Employing surfactant layer crystallization techniques as previously described, results were obtained with 10 mole percent of GM1 mixed with dioleoylphosphatidylethanolamine, a concentration of GM1 approximately that required to bind all B subunits in the arrays of cholera toxin described later.

Surfactant solution [1 μl of chloroform:hexane, 1:1 by volume, containing 0.1 mg/ml GM1 (Supelco) and 0.4 mg/ml dioleoylphosphatidylethanolamine (Avanti Polar Lipids, Inc.)] was applied to the surface of 50 μl of protein solution [250 μl/ml cholera toxin (Sigma Chemical Co.) in 0.2M sodium borate, pH 8.2 or 0.01M Tris/HCl, pH 7.2–0.5M NaCl] in a Teflon trough (5×10 mm, 1 mm deep). Alternatively, protein solution (10 μl, 1 mg/ml) was injected beneath preformed surfactant layers, with essentially the same results. Following incubation in a humid atmosphere at room temperature, carbon-coated electron microscope grids were brought in contact with the film in the trough, withdrawn, washed with a drop of water or buffer solution, and stained with 1% uranyl acetate. The cholera toxin used in these experiments was analyzed in SDS-polyacrylamide gels, before and after treatment with 2-mercaptoethanol. The results showed that less than 10% of the material was in a reduced state before mercaptoethanol treatment, and 95% or more was proteolytically cleaved (releasing free A1 upon reduction).

Following a period of incubation, areas of the surfactant film and associated protein crystals were recovered for viewing by placing a carbon-coated electron microscope grid on the film and withdrawing it. The hydrophobic layer of carbon retained the film in a known orientation, with the hydrocarbon chains of the surfactants abutting the grid. Protein exposed on the surface was negatively stained with uranyl acetate.

Cholera toxin formed arrays up to 100μ across with a high degree of order in some areas, during incubations of 6–64 h at room temperature, under physiologic conditions of pH and ionic strength. Optical diffraction from electron micrographs revealed both rectangular and hexagonal crystal lattices, isomorphous with those previously obtained for the B oligomer. Treatment of cholera toxin crystals with dithiothreitol to cleave the disulfide bond in the A subunit (and release active A1 fragment), did not affect the crystal lattices but did alter many intensities in the diffraction pattern indicative of a change in molecular structure.

Projected Structures and Difference Maps

Rectangular lattices of the B oligomer, complete toxin, and activated toxin were used to derive structural information. In all three cases, diffraction extended to a ninth order reflection at 15 $Å^{-1}$, the approximate limit of resolution for specimens in negative stain. Several images of each form of the toxin were processed by standard methods (Amos, et al., 1982, supra) (Table 1). Average Fourier transforms were refined to a common p2 phase origin and used to calculate projected structures.

TABLE 1

Image Processing of Electron Micrographs

| | B oligomer | complete toxin | reduced toxin |
|---|---|---|---|
| Projected structures | | | |
| Number of images averaged | 6 | 6 | 4 |
| Average phase error/image | 11.5° | 12.5° | 13.1° |
| Number of Fourier terms | 60 | 50 | 40 |
| Symmetry imposed | p2 | p2 | p2 |
| Three-dimensional structures | | | |
| Number of images | 26 | 19 | 10 |
| Average phase error/image | 19 | 22.9 | 21.2 |
| Number of Fourier terms | 207 | 156 | 142 |
| Number of independent lattice lines | 52 | 39 | 39 |
| Range of tilt angles | 0–52° | 0–52° | 0–52° |
| Summetry imposed | p21 | p21 | p21 |

In all cases, a unit cell of the projected structure (dimensions a=120 Å, b=131 Å, γ=90°) contains four pentagonally shaped regions of protein density. In the B oligomer structure, this density is concentrated in a ring of five peaks around a central channel. In the complete toxin, the size of the pentagonal region is the same, but the central channel is filled with additional density and the surrounding peaks are obscured. Finally, the structure of the activated toxin appears intermediate between those of the B oligomer and the complete toxin.

The location of additional density in the complete and activated toxins was clearly revealed by the calculation of difference maps. Average Fourier components determined for the B oligomer were subtracted from those for the complete and activated toxins. Difference density distributions were obtained, with four peaks in the unit cell which, when superimposed on the B oligomer, lay directly over the central channel. The strength of the difference peaks was twice as great for the complete toxin as for the activated toxin. These findings are consistent with a central location of the A1 fragment of the A subunit, as further shown by three-dimensional structure determination.

Three-dimensional Structure

Images of tiled specimens were analyzed at resolutions of about 20 Å for the B oligomer and the complete toxin and about 25 Å for the activated toxin (Table 1). Images were recorded at 100 kV at a magnification of 36,000× with a Philips EM400 electron microscope (underfocused 300–8000 Å), using minimal electron doses (10–15 electrons/$Å^2$ for each image). Images were densitometered using a step and sampling size of 20 um. Data sets, combined in three-dimensional analysis by standard methods, contained the same diffraction maxima and gave average phase errors upon origin refinement of less than 30°. Tilt axes and angles were calculated from distortions of the reciprocal lattices. Average data from untilted specimens served as initial sets for refinement of data from tilted specimens (according to the 2-sided plane group p21), which was carried out with a comparison range in $Z^*$ of 0.0083 $Å^{-1}$. Terms along the (0,0) lattice lines were not included. Continuous curves were fitted to the experimental points along each lattice line, and the curves were then sampled at intervals of 0.01 $Å^{-1}$.

The three-dimensional density distributions of the B oligomer structure clearly reveal a ring of five barrel-shaped objects which may be interpreted as individual subunits. The objects, on average, measure about 25 by 40 Å when contoured at a level which accounts for 95% of the mass of the B subunit (density 1.31 g/cc). The variable orientation of the subunits, either standing on end or tilted with respect to the membrane surface, may not be significant at the resolution of this analysis.

Comparison of the three-dimensional structures of the complete toxin and B oligomer confirms and extends conclusions drawn from the projection maps. The shape and dimensions of the two structures are nearly identical, except in the central channel, where there is extra density in the complete toxin. The correspondence of external features in the two structures indicates that the arrangement of B subunits is the same, so the extra density in the complete toxin must be due to the A subunit. The strength of the extra density is comparable to that elsewhere in the structure, but this density only partially fills the central channel, giving the toxin a puckered appearance on the face opposite the membrane surface. The volume of the extra density represents less than one-third of that expected from the mass of the A subunit. Continuity of the missing density with that in the channel is only possible beneath and not above the membrane surface. That is, the majority of the A subunit, about 18 kd, must lie within the hydrophobic interior of the surfactant membrane, inaccessible to the negative stain outlining the structure. A sphere of this mass would be about 35 Å in diameter, and so would nearly span a surfactant bilayer membrane.

The change in three-dimensional structure of the toxin that occurs upon activation by chemical reduction fits with the assignment of the density to subunits discussed above. Approximately 75% of the density in the central channel disappears upon reduction, leaving a residuum of about 2.5 kd, located near the base of the channel. The rest of the structure is virtually identical to that of the B oligomer. Since reduction releases the A1 fragment, the resulting loss of density from the central channel confirms the location of the A subunit within the channel. The density that remains is comparable to that expected for the A2 fragment (5 kd), but it could also represent a vestige of the A1 fragment. Whatever the origin of the residual density, its distribution around the perimeter of the channel may be a consequence of averaging over many molecules in the crystal, with the A1 and A2 fragments presumably occupying any one of five equivalent positions in the channel.

Studies of Monoclonal Antibodies

Using pure surfactant-hapten films and a range of solution conditions (as described previously), including physiologic pH and ionic strength, monoclonal anti-dinitrophenyl IgG formed two types of crystal, one hexagonal and the other linear. The hexagonal lattice ordered to a resolution of 20 Å in negative stain, and was suitable for preliminary three-dimensional image analysis. The linear lattices, apprently rows of antibodies, were less ordered than the hexagonal arrays. The linear arrays exhibited two predominate side-by-side periodicities, one about 250 Å and the other about 150 Å. Often the two linear lattices merged to form continuous rows.

Figure 4:
FIG. 4 is an electron micrograph of antibody bound surfactant-hapten layers titrated with other filler surfactants (phospholipids) resulting in linear tubes about 400–600 Å in diameter. Negative stain outlines a central channel which runs the length of each tube.

Systematic studies on the physical state and composition of the surfactant layers revealed several properties critical for two-dimensional crystallization. First, antibody ordering required that the surfactant-hapten be in a fluid state surfactant layer, suggesting that surfactant diffusion may be one mechanism for facilitating lattice formation. Surfactant-hapten in a crystalline state bound antibody but no protein ordering occurred. Second, the fluid state films must be near their maximum equilibrium spreading pressure. Surfactant-hapten films maintained at low surface tension yielded few order protein arrays. Finally, titrating the surfactant-hapten layers with other phospholipids (filler surfactants) gave rise to an altogether different type of ordering, linear tubes about 400–600 Å in diameter packed tightly into parallel arrays. Micrographs of tubes which had been dehydrated and shadowed with carbon/platinum revealed a linear micellular structure. Negative stain outlined a central channel which runs the length of each tube. (FIG. 4)

The lateral surface tension of the surfactant layers exerted similar effects on crystallization of antibodies, ribonucleotide reductase and cholera toxin. In contrast, the concentration of surfactant-ligand in the surfactant layers or type of filler surfactants comprising them had varying effects on array formation among the different proteins.

Extending these structural studies to a higher resolution prompted the need for larger more intact crystalline domains. However, the two-dimensional crystals formed by surfactant layer crystallization (LLC) often shattered, folded or distorted due to shearing forces during transfer to solid supports. One solution to this problem was demonstrated by the use of films with polyerizable fatty acids as fillers instead of phospholipids. These films facilitated cholera toxin ordering and upon polymerization, stabilized the crystals. Thin crystalline plates of fatty acid doped with ganglioside were grown at the air/water interface, treated with toxin for a period of time, then polymerized by irradiation. Intact platelets, often over 10 microns in length and several microns wide, resisted shear during transfer to electron microscope grids. Polymerized monolayers of pure fatty acid showed similar stabilities (Day and Lando, *Macromolecules* (1980) 13:1478–1483; Day and Lando, *Ibid* (1980) 13:1483–1487).

The procedure employed for preparing the surfactant layer and binding the protein was analogous to the previous procedures. A solution of 10 mole percent GM1 and 90 mole percent tricosa-10,12-diynoic acid in $CHCl_3$:hexane (1:1) with a trace amount of methanol to solubilize GM1 (0.1–0.5 mg of surfactant/ml) was spread over buffer (Tris or borate as described previously) in Teflon, PVC or Delrin plastic wells. Mono- or multi-layers of surfactants could be formed depending on the amounts applied to the surface. A concentrated solution of the protein was then injected below the surfactant layers into the buffer (15 $\mu l$) to a final concentration of 50–250 $\mu g$/ml. The film pressure was monitored to maintain the maximum equilibrium spreading pressure and sufficient time was allowed for binding and ordered of the protein layer. Polymerization was achieved with short-wave ultra-violet light (254±nm) irradiating for about 1 to several minutes. Thick layers appeared blue. Alternatively, similar results were obtained where polymerization was performed prior to the injection of the protein. A carbon-coated EM grid (with carbon touching hydrophobic tails of the surfactant) was contacted to the air/water interface, removed and stained.

The toxin ordered to an even greater extent on polymerized films than on phospholipid films. Fatty acid/GM1 platelets though often multilayered, bound protein primarily on the outer leaflet with no protein integrating between layers. These findings suggest that in contrast to surfactant diffusion as a mechanism of protein crystallization, specific binding to constrained crystalline surfaces may also promote protein ordering, a mechanism reminiscent of epitaxial crystal growth observed in some organic materials.

Figure 5:
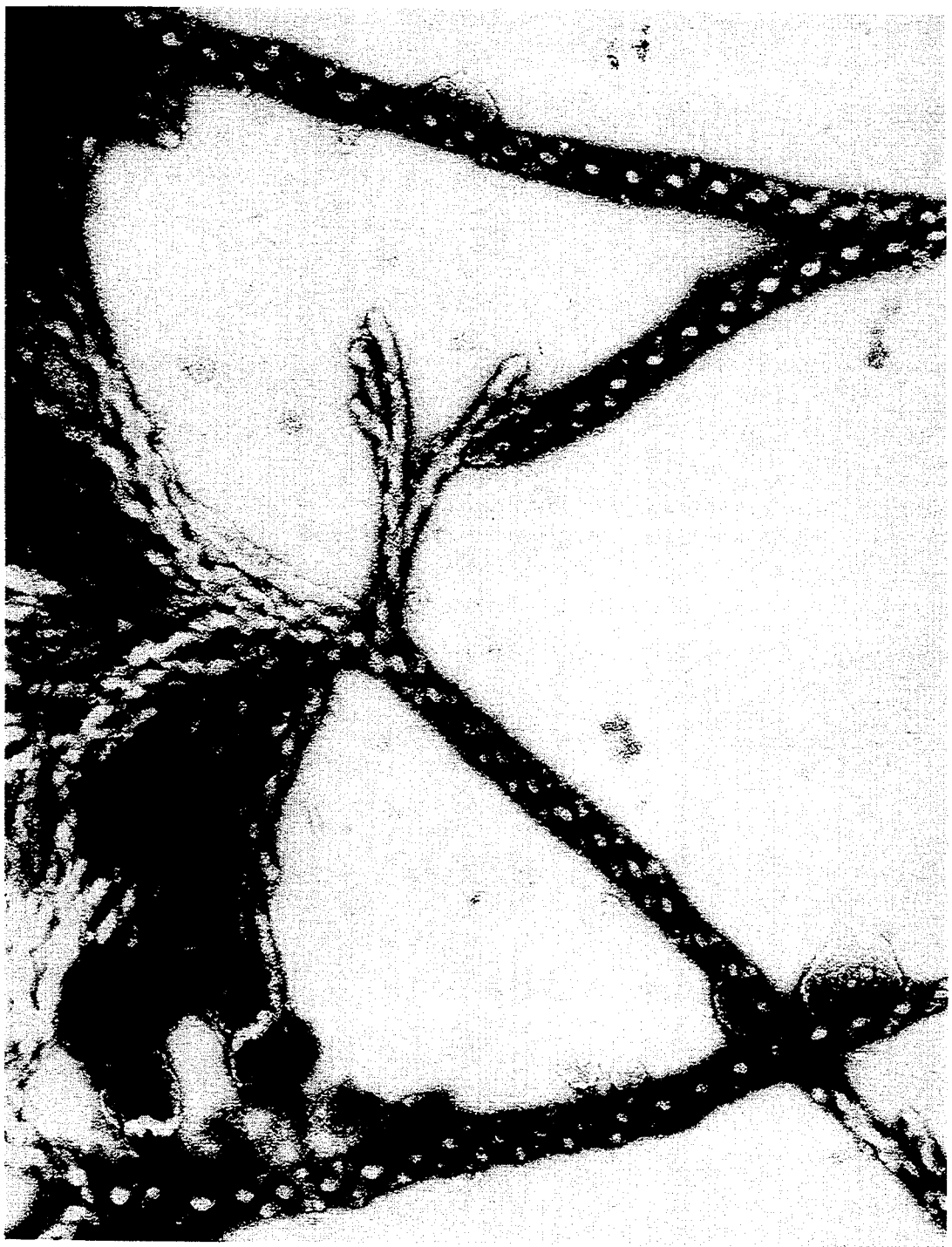
FIG. 5 is an electron micrograph depicting intricately braided helical wires tightly wound at the stem, branching along the length and splaying out at the ends, resulting from the addition of multivalent cations to the protein solution.

As with the previous examples discussed, complex three-dimensional assemblies of toxin bound to fatty acid films also form. Addition of polyvalent cations (e.g. spermidine or spermine, 10 mM final concentration) to the solution yielded intricately braided helical wires, tightly wound at the stem branching along the length, splaying out at the ends like unraveling pieces of rope. (FIG. 5) While the lengths varied between a fraction of a micron to several microns, there were only two predominant thicknesses, one about 800 Å and the other about 400 Å. Planar two-dimensional crystals of protein bound polymer with filamentous polymer threads extending away from the crystalline region were also formed using similar conditions.

It is obvious from the above results, that by employing polymerized surfactant layers, a number of advantages ensue. First, more stable articles are obtained, which allow for ease of structural determination. Second, depending upon the conditions, various conformations can be obtained, such as multilamellar structures, tubular structures or helical structures. These structures can find a wide variety of applications in electronics and biosensors as evidenced by polymerized surfactant monolayers and multilayers in MIS switches, FETs and the like.

Although the foregoing invention has been described in some detail by way of illustration and example for purposes of clarity of understanding, it will be obvious that certain changes and modifications may be practiced within the scope of the appended claims.

What is claimed is:

1. An article comprising a solid support, at least one addition polymerized surfactant monolayer having polymeric strands in a substantially ordered array coated thereon, said surfactant monolayer(s) having been polymerized from surfactant monomers having an aliphatic chain comprising a polymerizable functionality, and an ordered protein layer being capable of producing an optical diffraction pattern bound to said surfactant monolayer(s).

2. An article according to claim 1, wherein said solid support is a semiconductor.

3. An article according to claim 2, wherein said semiconductor is a doped silicon.

4. The article of claim 1, wherein said polymerizable functionality is separated from either termini of said aliphatic chain by at least one carbon atom.

5. An article as in claim 4, wherein said surfactant monomers have aliphatic chains comprising polymerizable diynes.

6. An article as in claim 1 wherein said protein layer is bound to said surfactant monolayer(s) by way of interaction between said protein and a ligand for said protein attached to said surfactant monolayer(s).

* * * * *